United States Patent [19]

Stohl et al.

[11] Patent Number: 4,572,184
[45] Date of Patent: Feb. 25, 1986

[54] WAVE GUIDE ATTACHMENT MEANS AND METHODS

[75] Inventors: Clark E. Stohl, Lakewood; Eugene DeCastro, Jamestown, both of N.Y.

[73] Assignee: Blackstone Corporation, Jamestown, N.Y.

[21] Appl. No.: 546,330

[22] Filed: Oct. 28, 1983

[51] Int. Cl.⁴ .............................................. A61B 17/00
[52] U.S. Cl. .................................... 128/328; 310/323; 310/325
[58] Field of Search ............... 128/328, 24 A; 604/22; 310/323, 325; 333/254, 255

[56] References Cited

U.S. PATENT DOCUMENTS 4,127,125 11/1978 Takemoto .................... 128/24 A
4,486,680 12/1984 Bonnet et al. .................... 128/328

Primary Examiner—Gene Mancene
Assistant Examiner—Cary E. Stone
Attorney, Agent, or Firm—Buell, Ziesenheim, Beck & Alstadt

[57] ABSTRACT

A transducer, wave guide and attachment means are provided as a screw member adapted to fit in a threaded opening in a transducer and having a tool engaging head at one end, an axial passage therethrough, a recess around the axial passage at the end opposite the tool engaging head, a wave guide slip fitted in the passage with a solidified bonding mass such as braze alloy or solder around the end of the wave guide in the recess.

11 Claims, 3 Drawing Figures

WAVE GUIDE ATTACHMENT MEANS AND METHODS

This invention relates to wave guide attachment means and methods and particularly to means and method for the attachments of one end of a long wave guide to a power source such as an ultrasonic transducer.

There are a number of machines and operations where it is desirable to couple one end of an elongate wave guide or wire to a power source such as an ultrasonic transducer so that working energy is transmitted along the wave guide from the ultrasonic transducer to a work piece. One such typical machining operation is illustrated in U.S. Pat. No. 3,830,240 entitled METHOD AND APPARATUS FOR DISINTEGRATING URINARY CALCULI. In that apparatus and method it is necessary to produce lateral and/or longitudinal vibrations at frequencies above 20 KHZ along a wave guide from an ultrasonic transducer to a calculi to be machined or disintegrated in a ureter. The wave guides (wires) are constructed of high endurance alloys to provide maximum life and minimum breakage. Prior art practice has been to insert the wave guide into a hole in the tip of the ultrasonic transducer and secure the same with a set screw. This, however, results in a stress concentration at the set screw and subsequent breakage of the wire. The wire is also deformed by pushing it to one side of the hole which also causes fretting and subsequent breakage at the exit opening. This results in two problems; premature breakage of the wave guide and difficulty in removing the broken piece of wave guide in the opening of the hole in the ultrasonic transducer.

In an effort to overcome this problem it has been proposed to use two opposing set screws, one having a groove machined in the face to receive the wave guide and act as an anvil against which the wave guide (wire) is clamped by the other set screw. This prevents bending of the wire in the hole and has resulted in an increased life of about 30%. However, the broken piece is still difficult to remove and the life expectancy too short.

The present invention provides an attachment means which further improves the time to failure over the improved two set screw system by 200% or more and eliminates the problem of removal of the broken piece.

We provide a wave guide and attachment in the form of a screw having a tool engageable head, an axial passage through the screw providing a slip fit with the wave guide, a recess around the passage at the end opposite the tool engageable head and a solidified fastening mass around one end of the wave guide in said recess fixing the wave guide therein. Preferably, the fastening mass is a metallurgical bonding material such as braze alloy or solder. The wave guide is preferably a cobalt base alloy. Preferably, the screw is provided with a hex head for engagement with a wrench. The wave guide is assembled to a transducer by screwing the threaded end into a threaded opening in the tip of a standard ultrasonic concentrator horn for application of ultrasonic energy to the wave guide.

In manufacturing the attachment and wave guide by metallurgical bonding it is necessary to prevent the portion of the wave guide protruding from the head of the screw from reaching a critical temperature. In order to accomplish this the recess is fluxed, heated and filled with braze alloy or solder while the wave guide protruding from the face of the screw at the head end is heat sinked to prevent the temperature from rising excessively. With this structure and method the metallurgically bonded portion of the wave guide and the portion next adjacent to it is constrained against lateral vibration by the slip fit hole in which it is fitted.

In the foregoing general description of our invention we have set out certain preferred practices and embodiments of this invention. Other objects, purposes and embodiments of the invention will be apparent from a consideration of the following description and the accompanying drawings in which.

Figure 1:
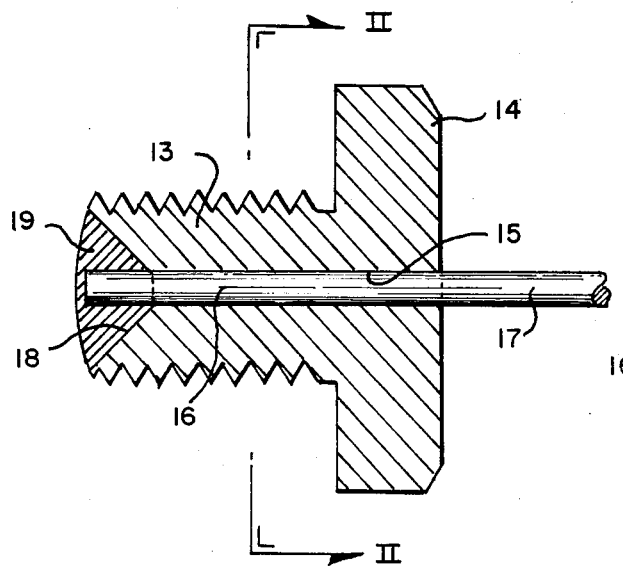
FIG. 1 is a longitudinal section of the attached end and attachment for a wave guide according to this invention.
Figure 2:
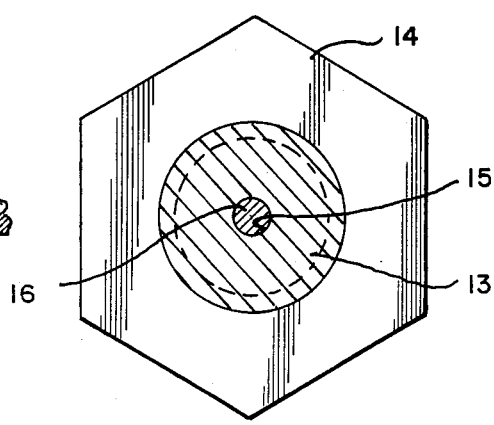
FIG. 2 is a section on line II—II of FIG. 1.
Figure 3:
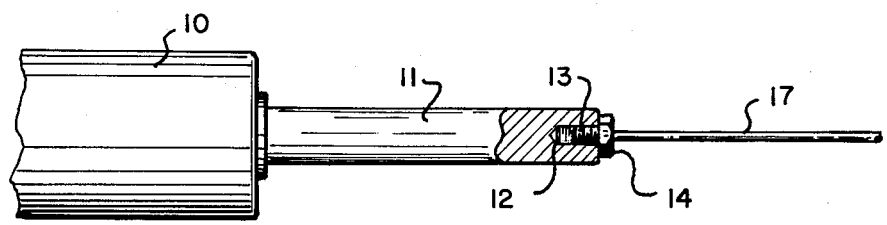
FIG. 3 is a section through a typical transducer concentrator horn with the wave guide and attachment in place.

Referring to the drawings we have illustrated an ultrasonic transducer 10 having a concentrator horn 11 with a threaded opening 12 receiving a screw 13 having a hexagonal head 14 by means of which the screw is tightly fastened in threaded opening 12. An axial passage 15 is provided in screw 13 to slip fit over the end 16 of wave guide 17. A cup shaped recess 18 is provided in the end screw 13 opposite head 14. This recess 18 is filled with a metallurgical bonding agent 19 such as braze alloy or solder, bonded to the end 16 of wave guide 17 and to the walls of recess 18, to fix the wave guide to the screw.

The portion of the wave guide which is affected by the metallurgical bond is effectively that portion surrounded by the braze metal or solder and a short adjacent portion, all of which is rigidly supported against lateral vibration and thus protected against breakage by such lateral vibration. The balance of the wave guide is unaffected by the metallurgical bond and is free from pressure induced deformities such as produced by set screws. If the wave guide breaks, the attaching end is unscrewed and a new wave guide inserted.

In the foregoing specification we have set out certain preferred practices and embodiments of this invention, however, it will be understod that this invention may be otherwise embodied within the scope of the following claims.

We claim:

1. In combination a transducer, wave guide and attachments comprising a transducer having a concentrator horn attached thereto at one end, a threaded opening in said horn at the opposite end thereof, a screw member having a tool engageable head for threading said screw member into the threaded opening in the horn, a single wave guide, an axial passage through the screw providing a slip fit with the single wave guide, a recess around the passage at the end opposite the tool engaging head and a solidified fastening mass around one end of the wave guide in said recess fixing the said end of the wave guide therein.

2. A transducer, wave guide and attachment means as claimed in claim 1 wherein the tool engageable head is a hexagonal shaped head.

3. A transducer, wave guide and attachment means as claimed in claim 1 or 2 wherein the fastening mass is a metallurgical bonding material.

4. A transducer, wave guide and attachment means as claimed in claim 3 wherein the metallurgical bonding material is a braze alloy.

5. A transducer, wave guide and attachment means as claimed in claim 3 wherein the metallurgical bonding material is solder.

6. A wave guide assembly for threaded attachment to a transducer horn spaced from the transducer comprising a screw member having a tool engageable head, a wave guide, an axial passage through the screw providing a slip fit with the wave guide, a recess around the passage at the end opposite the tool engaging head and a solidified fastening mass around one end of the wave guide in said recess fixing the said end of the wave guide therein.

7. A wave guide assembly as claimed in claim 6 wherein the tool engageable head is a hexagonal shaped head.

8. A wave guide assembly as claimed in claim 6 or 7 wherein the fastening mass is a metallurgical bonding material.

9. A wave guide assembly as claimed in claim 8 wherein the metallurgical bonding material is a braze alloy.

10. A wave guide assembly as claimed in claim 8 wherein the metallurgical bonding material is solder.

11. A method of forming a wave guide assembly for threaded attachment to a transducer horn spaced from the transducer comprising the steps of:
 (a) forming a screw member with a tool engageable head at one end and an axial passage therethrough adapted to receive a wave guide with a slip fit;
 (b) forming a recess in the screw member around the axial passage at the end opposite the tool engageable head;
 (c) inserting one end of a wave guide through the axial passage into the recess;
 (d) fluxing, heating and filling the recess with a metallurgical bonding material around the said one end of the wave guide while heat sinking the wave guide at the opposite end of the passage in the screw; and
 (e) cooling said metallurgical bonding material in said recess to bond the same to the recess and said one end of the wave guide.

* * * * *